United States Patent [19]

Krapcho et al.

[11] Patent Number: 4,578,474

[45] Date of Patent: Mar. 25, 1986

[54] IMIDO, AMIDO AND AMINO DERIVATIVES OF MERCAPTOACYL PROLINES AND PIPECOLIC ACIDS

[75] Inventors: John Krapcho, Somerset; Peter C. Wade, Pennington, both of N.J.

[73] Assignee: E. R. Squibb & Sons, Inc., Princeton, N.J.

[21] Appl. No.: 672,977

[22] Filed: Nov. 19, 1984

Related U.S. Application Data

[62] Division of Ser. No. 454,936, Jan. 3, 1983, Pat. No. 4,497,953, which is a division of Ser. No. 268,921, Jun. 1, 1981, Pat. No. 4,390,695, which is a division of Ser. No. 162,341, Jun. 23, 1980, Pat. No. 4,310,461.

[51] Int. Cl.[4] .................. C07D 401/04; C07D 403/04
[52] U.S. Cl. .................................... 546/188; 546/208; 546/210; 546/99; 546/198; 546/200; 548/336; 548/518; 548/465

[58] Field of Search ................ 546/188, 210, 208; 548/336, 518

[56] References Cited

U.S. PATENT DOCUMENTS 4,105,776 8/1978 Ondetti et al. ...................... 548/518
4,154,935 5/1979 Ondetti et al. ...................... 548/518

FOREIGN PATENT DOCUMENTS 2028327 3/1980 United Kingdom ................ 548/518

*Primary Examiner*—Robert T. Bond
*Attorney, Agent, or Firm*—Lawrence S. Levinson; Donald J. Barrack

[57] ABSTRACT

Imido, amido and amino derivatives of mercaptoacyl prolines and pipecolic acids are useful for the treatment of hypertension.

12 Claims, No Drawings

IMIDO, AMIDO AND AMINO DERIVATIVES OF MERCAPTOACYL PROLINES AND PIPECOLIC ACIDS

This is a division of application Ser. No. 454,936, filed Jan. 3, 1983, now U.S. Pat. No. 4,497,953 which is a division of application Ser. No. 268,921, filed June 1, 1981, now U.S. Pat. No. 4,390,695, issued June 28, 1983, which is a division of application Ser. No. 162,341, filed June 23, 1980, now U.S. Pat. No. 4,310,461, issued Jan. 12, 1982.

BACKGROUND OF THE INVENTION

The recent literature discloses a variety of mercaptoacyl amino acids which are useful for inhibiting the conversion of angiotensin I to angiotensin II in mammals, and are, therefore, useful in the treatment of hypertension.

U.S. Pat. No. 4,105,776, issued Aug. 8, 1979 discloses mercaptoacyl amino acids wherein the amino acid is, inter alia, proline, 4-hydroxyproline and 4-alkylproline.

U.S. Pat. No. 4,154,935, issued May 15, 1979 discloses mercaptoacyl amino acids wherein the amino acid is, inter alia, 4-halogen substituted proline, or 4,4-dihalogen substituted proline.

BRIEF DESCRIPTION OF THE INVENTION

Compounds having the formula

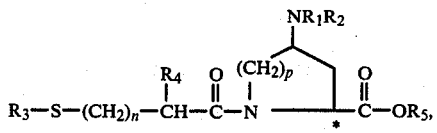

and salts thereof, and the symmetrical dimer thereof, inhibit the action of angiotensin converting enzyme, and are, therefore, useful for the treatment of hypertension. In formula I, and throughout the specification, the symbols are as defined below.

$R_1$ and $R_2$ are the same or different and are hydrogen, alkyl, cycloalkyl, 1-adamantyl, aryl, arylalkyl, alkylcarbonyl, arylcarbonyl, arylalkylcarbonyl, alkylsulfonyl, arylsulfonyl, or arylvinylcarbonyl (aryl-CH=CH—CO—), or together with the nitrogen atom to which they are attached $R_1$ and $R_2$ are 1-pyrrolidinyl, 1-piperidinyl, 1-homopiperidinyl, 4-morpholinyl, 4-alkyl-1-piperazinyl, 4-aryl-1-piperazinyl, 1-imidazolyl, 1-pyrrolidinyl-2,5-dione(succinimido), 3-alkyl-1-pyrrolidinyl-2,5-dione, 3-aryl-1-pyrrolidinyl-2,5-dione, 1-piperidinyl-2,6-dione, 3-alkyl-1-piperidinyl-2,6-dione, 3-aryl-1-piperidinyl-2,6-dione, 2H-isoindol-2-yl-1,3-dione (phthalimido), hexahydro-2H-isoindol-2-yl-1,3-dione (hexahydrophthalimido), 2,5-dihydro-2,5-dioxo-1H-pyrrol-1-yl(maleimido), 1,1,3-trioxo-1,2-benzisothiazol-2(3H)-yl(2-saccharinyl), or 1,3-dihydro-1,3-dioxo-2H-benz[de]isoquinolin-2-yl(1,8-naphthalenedicarboximido);

$R_3$ is hydrogen, alkyl, aryl, arylalkyl, or a hydrolyzable acyl protecting group such as alkanoyl or arylcarbonyl;

$R_4$ is hydrogen, alkyl, alkylthio, or trifluoromethyl;
$R_5$ is hydrogen, alkyl, or arylalkyl;
n is 0, 1 or 2; and
p is 1 or 2.

The term "aryl", as used throughout the specification either by itself or as part of a larger group, refers to phenyl, 1-naphthyl, 2-naphthyl or phenyl substituted with halogen, alkyl, alkoxy, alkylthio, hydroxy, alkanoyl, nitro, amino, dialkylamino, phenyl or trifluoromethyl groups. Phenyl and monosubstituted phenyl are the preferred aryl groups; phenyl is the most preferred group.

The term "cycloalkyl", as used throughout the specification either by itself or as part of a larger group, refers to cycloalkyl groups having 3 to 7 carbon atoms.

The term "alkyl", as used throughout the specification either by itself or as part of a larger group, refers to groups having 1 to 8 carbon atoms. Alkyl groups having 1 to 3 carbon atoms are preferred.

The term "alkoxy", as used throughout the specification either by itself or as part of a larger group, refers to groups having 1 to 8 carbon atoms. Alkoxy groups having 1 to 3 carbon atoms are preferred.

The term "halogen", as used throughout the specification either by itself or as part of a larger group, refers to fluorine, chlorine, bromine and iodine. The preferred halogen groups are fluorine and chlorine.

The term "alkanoyl", as used throughout the specification either by itself or as part of a larger group, refers to groups having up to 9 carbon atoms.

The asterisk in formula I indicates a center of asymmetry in the ring. In the instance wherein the ring is proline (p is 1) this asymmetric center is in the L-configuration. In the instance wherein the ring is pipecolic acid (p is 2) this asymmetric center is in the DL- or L-configuration.

The carbon atom to which the group $NR_1R_2$ is attached is another asymmetric center. Depending on the definition of $R_4$, the sulfur containing side-chain may also contain an asymmetric center. The product of formula I, therefore, exists in stereoisomeric forms and as racemic mixtures thereof. All are within the scope of this invention. The synthesis described below can utilize the racemate or one of the enantiomers as starting materials. When one of the starting materials is chiral and the other is racemic, the stereoisomers obtained in the final product can be separated by conventional chromatographic or fractional crystallization methods. Preferably, if there is an asymmetric center in the sulfur containing side-chain, it is in the D-configuration.

DETAILED DESCRIPTION OF THE INVENTION

The compounds of formula I, and salts thereof, and the dimer thereof, are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of the compounds of this invention, angiotensin dependent hypertension in the species of mammal (e.g., humans) suffering therefrom is alleviated. A single dose, or preferably two to four divided daily doses, provided on a basis of about 0.1 to 100 mg. per kilogram of body weight per day, preferably about 1 to 15 mg. per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 300 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorthiazide, hydrochlorthiazide, flumethiazide, hydroflumethiazide, bendroflumethiazide, methychlothiazide, trichlormethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration or in sterile solutions of suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of this invention can be prepared using 4-hydroxy-L-proline or 4-hydroxypipecolic acid as the starting material. In converting these 4-hydroxy compounds to the corresponding 4-amino, amido or imido compounds it is necessary to first protect the nitrogen atom and the carboxyl group. A protecting group such as carbobenzyloxy, tosyl, acetyl, benzoyl, etc., can first be attached to the nitrogen atom. For example, as described in the literature (see *Journal of the American Chemical Society*, 86, 4709 (1964)), 4-hydroxy-L-proline can be reacted with p-toluenesulfonyl chloride to yield 4-hydroxy-1-[(4-methylphenyl)sulfonyl]-L-proline. The carboxyl group of the 4-hydroxy-N-tosyl-L-proline or pipecolic acid can be protected by esterification, e.g., by reaction with a diazoalkane (see *Journal of the American Chemical Society*, 79, 191 (1957)).

The 4-hydroxy substituent of the resulting 4-hydroxy-N-tosyl-L-proline or pipecolic acid ester can be converted to a leaving group using art-recognized procedures. For example, reaction of the 4-hydroxy compound with p-toluenesulfonyl chloride following the procedure described in the *Journal of the American Chemical Society*, 79, 191 (1957) yields 4,N-ditosyl-L-proline, alkyl ester.

Displacement of the 4-protecting group with a compound having the formula $$HNR_1'R_2',$$ II or an alkali metal salt thereof, is accomplished with inversion of the stereoisomerism of the compound. Therefore, if 4-trans-hydroxyproline is used as the starting material the product will have the cis configuration, and if 4-cis-hydroxyproline is used as the starting material the product will have the trans configuration. The resulting compound will have the formula

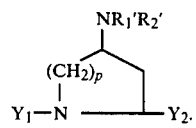
III

In formulas II and III, and throughout the specification, the symbols $R_1'$ and $R_2'$ have the same definitions as $R_1$ and $R_2$ respectively, except $R_1'$ and $R_2'$ cannot both be hydrogen; the symbols $Y_1$ and $Y_2$ are a protecting group and a protected carboxyl group respectively.

Prior to acylating an intermediate of formula III to obtain a product of formula I, the protecting group is removed from the nitrogen atom and can optionally be removed from the carboxyl group. Techniques for deprotection are well known in the art. If the carboxyl group has been esterified to protect it, the protecting group can be removed using conventional saponification techniques. If the nitrogen atom has been protected with a tosyl group, that group can be removed by treating the compound with a solution of hydrogen bromide. The deprotected amino acid has the formula

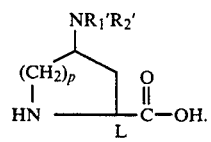
IV

The compounds of formula I ($R_1$ and $R_2$ other than hydrogen) can be obtained by acylating an intermediate of formula IV with an acid having the formula

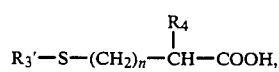
V wherein $R_3'$ is alkyl, aryl, arylalkyl or a hydrolyzable acyl protecting group. The acylation reaction is run in the presence of a coupling agent such as dicyclohexylcarbodiimide, or the acid can be activated by formation of its mixed anhydride, symmetrical anhydride, acid halide (preferably acid chloride) or acid ester, or by use of Woodward reagent K, N-ethoxycarbonyl-2-ethoxy-1,2-dihydroquinoline or the like. For a review of these methods of acylation reference can be made to *Methoden der Organischen Chemie* (Houben-Weyl), Vol. XV, part II, page 1 et seq. (1974).

To prepare a compound of formula I wherein $R_3$ is hydrogen, a corresponding product of formula I wherein $R_3$ is a hydrolyzable acyl protecting group can be treated with base, such as potassium hydroxide or ammonia, in water or other suitable solvent.

The compounds of this invention wherein one, or both, of $R_1$ and $R_2$ are hydrogen can be obtained from the corresponding product of formula I wherein one, or both, of $R_1$ and $R_2$ are phenylmethyl. The phenylmethyl group can be removed by treatment with sodium and liquid ammonia.

An alternative synthesis for the preparation of the compounds of this invention, wherein at least one of $R_1$ and $R_2$ is alkylcarbonyl, arylcarbonyl, arylalkylcarbonyl, alkylsulfonyl, arylsulfonyl or arylvinylcarbonyl also utilizes 4-hydroxy-L-proline or pipecolic acid as the starting material. The nitrogen atom is first protected, e.g., by reaction with benzyl chloroformate in the presence of an organic amine (e.g., triethylamine). The reaction can be run in an inert solvent and yields N-benzyloxycarbonyl-4-hydroxy-L-proline or pipecolic acid. Protection of the carboxyl group of the N-protected compound can be accomplished by reaction with a diazoalkane or by heating with benzyl chloride in the presence of an organic amine following the procedure described in the *Canadian Journal of Biochemistry and Physiology*, 37, 583 (1959). The resulting N-benzyloxycarbonyl-4-hydroxy-L-proline or pipecolic acid ester can be reacted with a compound having the formula $$HNR_1''R_2'' \qquad \qquad VI$$

in the presence of diethylazodicarboxylate and triphenylphosphine to yield N-benzyloxycarbonyl-4-($NR_1''R_2''$)-L-proline or pipecolic acid ester, which can in turn be deprotected by catalytic hydrogenation using, for example a palladium catalyst. Acylation of 4-($NR_1''R_2''$)-L-proline, or pipecolic acid (using the procedures described above for the acylation of an intermediate of formula III) yields the corresponding product of formula I. The symbols $R_1''$ and $R_2''$ are the same or different and are hydrogen, alkyl, cycloalkyl, 1-adamantyl, aryl, arylalkyl, alkylcarbonyl, arylcarbonyl, arylalkylcarbonyl, alkylsulfonyl, arylsulfonyl or arylvinylcarbonyl, with the proviso that at least one of $R_1''$ and $R_2''$ are one of the acyl or substituted sulfonyl groups.

A preferred synthesis for the products of formula I wherein $R_1$ and $R_2$ each is hydrogen comprises first preparing the corresponding product of formula I wherein $-NR_1R_2$ is phthalimido. Reaction of this product with hydrazine in an inert solvent yields the corresponding 4-amino product.

Still another procedure for preparing the compounds of this invention wherein $R_1$ is hydrogen and $R_2$ is alkylcarbonyl, arylcarbonyl, arylalkylcarbonyl or arylvinylcarbonyl comprises first preparing 4-azido-1-tosyl-L-proline or pipecolic acid (see the *Australian Journal of Chemistry*, 20, 1493 (1967)). This compound can be reduced using catalytic hydrogenation to obtain 4-amino-1-tosyl-L-proline or pipecolic acid, alkyl ester. Acylation of this compound yields the corresponding 4-acylamino-1-tosyl-L-proline or pipecolic acid, alkyl ester which can be deprotected and then acylated with an acid of formula V following the procedure described above.

Still another procedure for preparing the compounds of this invention utilizes the 4-hydroxyprolines or 4-hydroxypipecolic acids having the formula

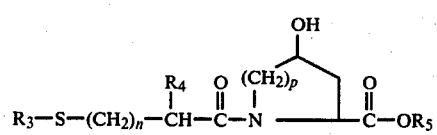

wherein $R_3$ and $R_5$ are other than hydrogen, as starting materials. The compounds of formula VII are disclosed in U.S. Pat. No. 4,105,776. Reaction of a compound of formula VII wherein the 4-hydroxyl group is first converted to a leaving group such as tosylate, methanesulfonate or triflate ($CF_3-SO_2$) with a compound of the formula $$HNR_1R_2, \qquad \qquad VIII$$

or a sodium or potassium salt thereof, gives the corresponding product of formula I.

Still another procedure for preparing the compounds of this invention wherein at least one of $R_1$ and $R_2$ is alkylcarbonyl, arylcarbonyl, arylalkylcarbonyl, alkylsulfonyl, arylsulfonyl or arylvinylcarbonyl comprises reacting a compound of formula VII with a compound of formula VI in the presence of triphenylphosphine and diethylazodicarboxylate.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The non-toxic, physiologically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

The symmetrical dimer of a product of formula I, i.e., compound having the formula

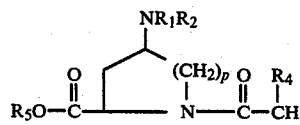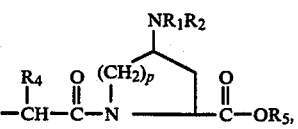

is also contemplated as an integral part of this invention. It is readily prepared from the corresponding product of formula I wherein $R_3$ is hydrogen by direct oxidation with iodine.

Compounds of formula I wherein p is 1 are preferred. Also preferred are compounds of formula I wherein n is 1 and $R_4$ is methyl.

The following examples are specific embodiments of this invention.

EXAMPLE 1

[1(S),4S]-4-(Benzoylamino)-1-(3-mercapto-2-methyl-1-oxopropyl)-L-proline (A)

(R)-4-Hydroxy-1-[(4-methylphenyl)sulfonyl]-L-proline

A stirred solution of 52.45 g (0.40 mole) of trans-4-hydroxy-L-proline in 500 ml of sodium hydroxide is treated with 85.79 g (0.45 mole) of p-toluenesulfonyl chloride in 500 ml of ether at room temperature. Stirring is continued for 6 hours, the layers are separated and the aqueous phase is cooled to 5° C. in an ice-bath. The mixture is then acidified while cooling with 30 ml of concentrated hydrochloric acid to pH 2 and the precipitated white solid is collected, washed with 150 ml of cold water, and dried in vacuo yielding 106.2 g of material, melting point 139°–143° C. Crystallization from 300 ml of ethyl acetate yields 98.6 g of the title compound, melting point 142°–145° C.

(B)

(R)-4-Hydroxy-1-[(4-methylphenyl)sulfonyl]-L-proline, methyl ester

The above N-tosyl-L-proline (24.25 g, 0.085 mole) is esterified with diazomethane in methanolether as described in *The Journal of the American Chemical Society*, 79, 191 (1957) yielding 25.3 g of product, melting point 101°–104° C.

(C)

(R)-1-[(4-Methylphenyl)sulfonyl]-4-[[(4-methylphenyl)sulfonyl]oxy]-L-proline, methyl ester A stirred solution of 23.95 g (0.08 mole) of the above trans-4-hydroxy-L-proline derivative in 50 ml of dry pyridine is treated dropwise at −5° C. to −8° C. with a solution of 17.16 g of p-toluenesulfonyl chloride (0.09 mole) in 20 ml of pyridine. The solution is stored in the cold room for 72 hours, added with stirring to 425 ml of ice-cold 2N hydrochloric acid, and the precipitated gum extracted with 200 ml of chloroform. The aqueous phase is extracted with additional chloroform (three 125 ml portions). The combined organic layers are dried (MgSO$_4$) and the solvent evaporated to give a viscous oil. The oil is dissolved in ethyl acetate (125 ml) and the product crystallized with cooling and rubbing to yield 26.8 g of trans-N,O-ditosylhydroxy-L-proline methyl ester, melting point 92°–94° C.

(D)

(S)-1-[(4-Methylphenyl)sulfonyl]-4-azido-L-proline,-methyl ester

A stirred solution of 22.68 g (0.05 moles) of the above trans-N,O-ditosylhydroxy-L-proline, methyl ester is dissolved in 150 ml of dimethylformamide, and 3.6 g (0.055 mole) of sodium azide in 17 ml of water is added. The reaction mixture is heated at 70° C. for 5 hours. It is cooled, and poured into a mixture of saturated brine (1000 ml) and water (200 ml), and extracted with ether (three 250 ml portions). The combined ether extracts are washed with saturated brine and dried (MgSO$_4$). Removal of the ether and crystallization of the residue from ether/light petroleum ether yields 12.4 g of the title cis-azide ester as needles, melting point 69°–70° C.

(E)

(S)-4-Amino-1-[(4-methylphenyl)sulfonyl]-L-proline, methyl ester

A solution of 9.73 g of the above cis-azide ester (0.03 mole) is dissolved in 100 ml of methanol and 1.0 g of 10% palladium on charcoal is added to the mixture. The mixture is hydrogenated for 6 hours at 50 psi. (The reaction bottle is flushed twice with hydrogen to remove the nitrogen as it is formed). The mixture is then filtered through Celite and the methanol removed in vacuo yielding 8.94 g of the amino product as a viscous oil. $[\alpha]_D^{26} - 50°(c=2,\text{MeOH})$.

(F)

(S)-4-(Benzoylamino)-1-[(4-methylphenyl)sulfonyl]-L-proline, methyl ester

A stirred solution of 8.95 g (0.03 mole) of the above cis-amino ester and 2.4 g (0.031 mole) of triethylamine in 100 ml of chloroform is cooled to 0° to 5° C. in an ice-bath and treated with 4.20 g (0.031 mole) of benzoyl chloride. The reaction is maintained under nitrogen and allowed to stir for about 16 hours at room temperature. The mixture is extracted with water (two 75 ml portions) followed by washing with 100 ml of a saturated salt solution. The chloroform solution is dried over anhydrous MgSO$_4$ and the chloroform removed in vacuo yielding a solid. Crystallization from 75% ethanol yields 10.46 g of the title compound, melting point 167°–169° C.

(G)

(S)-4-Benzoylamino-1-[(4-methylphenyl)sulfonyl]-L-proline

The above ester (10.0 g, 0.0248 mole) is dissolved in 120 ml of methanol, treated dropwise at 0° C. with 37.5 ml (0.0372 mole) of 2N sodium hydroxide kept at 0° C. for 1 hour, and at room temperature for about 16 hours. After removing about ½ of the solvent on a rotary evaporator, the solution is cooled and acidified with 6N HCl to pH 2, and extracted with four 150 ml portions of ethyl acetate. The combined extracts are washed with 100 ml of a saturated salt solution dried (MgSO$_4$) and the solvent evaporated to give 7.18 g of the title compound, melting point 120°–125° C. (sintering at 118° C.).

(H) (S)-4-(Benzoylamino)-L-proline, hydrobromide (1:1)

The above N-tosyl acid (7.0 g, 0.017 mole) and phenol (3.2 g, 0.035 mole) are treated with 28 ml of hydrogen bromide in acetic acid (30–32%), stoppered loosely, and stirred for 18 hours. Ether (300 ml) is added with swirling to the mixture and when the crystalline product has settled, the etheral liquor is decanted and the material is washed with 300 ml of fresh ether by decantation. The product is heated on the steam bath with 80 ml of methyl ethyl ketone, cooled, filtered, washed with cold methyl ethyl ketone and with ether, and dried in vacuo, yielding 2.6 g of the title compound, melting point 184°–188° C., dec.

(I)

(S),4S]-1-[3-(Acetylthio)-2-methyl-1-oxopropyl]-4-(benzoylamino)-L-proline

The above amino acid hydrobromide salt (2.6 g, 0.0078 mole) and 1.6 g of (0.0086 mole) of D-3-(acetylthio)-2-methylpropionyl chloride in 5 ml of ether are reacted in 50 ml of water in the presence of Na$_2$CO$_3$.

Initially, 2.4 ml of 25% Na$_2$CO$_3$ solution is required to obtain a pH of 8.0. Approximately 14 ml of 25% Na$_2$CO$_3$ (w/v) is consumed to stabilize the pH of 8.0–8.2 during the acylation (time approx. 45 minutes). The mixture is allowed to warm to room temperature and stirred for 1½ hours under argon. The mixture is worked up after an additional 1 hour by washing with 25 ml of ethyl acetate which is discarded, layered over with 25 ml of ethyl acetate, cooled, stirred, acidified carefully with 1:1 HCl to pH 2.0, saturated with salt and separated. The aqueous phase is extracted with three 25 ml portions of ethyl acetate, the combined organic layers are dried (MgSO$_4$) and the solvent removed in vacuo. The product is obtained as a syrupy oil, yield 2.30 g, which slowly begins to crystallize. The oil is treated in 30 ml of ethyl acetate with 1.5 g of dicyclohexylamine to give 2.18 g of the dicyclohexylamine salt of the title compound, melting point 160°–163° C., $[\alpha]^{26} -51°$ C. (c=1; methanol). Acidification of the dicyclohexylamine salt (2.18 g) with 26 ml of 10% KHSO$_4$ and extraction with 40 ml of ethyl acetate (four times) yields 1.1 g of the title compound, melting point 82°–84° C., $[\alpha]_D^{26} -81°$ (c=1; CHCl$_3$).

(J)

[1(S),4S]-4-(Benzoylamino)-1-(3-mercapto-2-methyl-1-oxopropyl)-L-proline

Argon is passed through a cold solution of 1.5 ml of concentrated ammonium hydroxide in 8.0 ml of water for 0.25 hours which is then added while cooling and under a blanket of argon to 1.0 g (0.0026 mole) of the above S-acetyl compound. The mixture is swirled in an ice-bath until a solution is obtained. Stirring under argon is continued at room temperature for an additional 2 hours, then the solution is extracted with 15 ml of ethyl acetate (this and subsequent operations are carried out as much as possible under an argon atmosphere). The aqueous layer is cooled, stirred, layered over with 15 ml of ethyl acetate and acidified portionwise with approximately 4.2 ml of 6N HCl. The layers are separated, the aqueous phase extracted with three 15 ml portions of ethyl acetate, the combined ethyl acetate layers dried (MgSO$_4$) and the solvent evaporated to give 0.46 g of the title compound after drying in vacuo, melting point 150°–152° C., $[\alpha]_D^{26} -44°$ (c=1; EtOH).

EXAMPLE 2

[1(S),4S]-1-[3-(Acetylthio)-2-methyl-1-oxopropyl]-4-(1,3-dihydro-1,3-dioxo-2H-isoindol-2-yl)-L-proline (A)
(S)-4-(1,3-Dihydro-1,3-dioxo-2H-isoindol-2-yl)-1-[(phenylmethoxy)carbonyl]-L-proline, phenylmethyl ester To a solution of 7.0 g of N-(benzyloxycarbonyl)-4-trans-hydroxy-L-proline, benzyl ester (described in Can. J. Biochem. & Phy., 37, 583 (1959)) 4.34 g of phthalimide, and 7.73 g of triphenylphosphine in 200 ml of dry (sieve) tetrahydrofuran is added 5.13 g of diethyl azodicarboxylate over 1 hour at room temperature. Thin layer chromatography (silica gel-ether) shows consumption of starting material is complete in less than two hours. The solvent is removed under vacuum and the residue diluted with 200 ml of ether. The resulting precipitate is filtered off and the filtrate is concentrated to about 40 ml. This material is flash chromatographed on silica gel with ether:pentane (1:1) to yield a total of 9.15 g of residue. The product is isolated in two fractions A (first portion eluted) and AA (second portion eluted). Both fractions are taken up in ether and allowed to stand. The resulting crystals are filtered off to yield the final product A$^1$ and AA$^1$. A$^1$ melts at 89°–90° C. while AA$^1$ melts at 117°–119° C., but on standing for several days the melting point changes to 89°–90° C., $[\alpha]_D^{25} -47.8°$ (a=0.5%;CHCl$_3$). Both fractions are identical chromatographically and spectrally (NMR) and are combined for further use.

(B)

[1(S),4S]-1-[3-(Acetylthio)-2-methyl-1-oxopropyl]-4-(1,3-dihydro-1,3-dioxo-2H-isoindol-2-yl)-L-proline A solution of 5.0 g of (S)-4-(1,3-dihydro-1,3-dioxo-2H-isoindol-2-yl)-1-[(phenylmethoxy)carbonyl]-L-proline, phenylmethyl ester in 200 ml of ethyl acetate and 100 ml of ethanol is hydrogenated with 2.0 g of 10% palladium on charcoal at room temperature and 40 psi. After 2 days the mixture is filtered to yield a mixture of the amino acid product and catalyst as the filter cake.

The mixture of catalyst and amino acid is suspended in 75 ml of dry pyridine and treated with 3 g of (S)-3-(acetylthio)-2-methylpropionyl chloride at room temperature. After 1 hour another 2 g of acid chloride is added. The mixture is stirred for 2 hours and filtered. The filtrate is evaporated to dryness and the residue partitioned between 1N HCl and ethyl acetate. The ethyl acetate solution is washed with water and saturated NaCl, dried (Na$_2$SO$_4$) and the solvents are removed under vacuum. The residue is chromatographed on silica gel with 7:1 toluene:acetic acid. The fraction with an R$_f$ of 0.1 (tlc) is collected and evaporated to dryness. The residue is taken up in ethyl acetate and filtered. The filtrate is again evaporated to dryness to yield 2.8 g of an oil. The oil is taken up in ether and allowed to stand for about 16 hours. The resulting crystals are filtered off and washed with ethyl acetate to yield the product, melting point 185°–188° C.; $[\alpha]_D^{25} -95.3°$ (c=1%;CHCl$_3$).

EXAMPLE 3

[1(S),4S]-4-Amino-1-(3-mercapto-2-methyl-1-oxopropyl)-L-proline

To 0.8 g of [1(S),4S]-1-[3-(acetylthio)-2-methyl-1-oxopropyl]-4-(1,3-dihydro-1,3-dioxo-2H-isoindol-2-yl)-L-proline suspended in 20 ml of methanol is added 36 drops of anhydrous hydrazine. After 30 minutes the mixture is concentrated to 5 ml and placed on a column of DEAE Sephadex which is eluted with a 0.005M to 0.5 molar gradient of aqueous ammonium carbonate. The fractions giving a positive sulfhydryl test (nitroprusside solution) are combined and lyophilized to yield the partially purified product. Further purification is achieved by chromatography on silica gel and elution with butanol:acetic acid:water (4:1:1).

EXAMPLES 4–17

Following the procedure of Example 2, but substituting the compound listed in Column I for phthalimide, yields the compound listed in Column II.

| Columm I | Column II |
| --- | --- |
| 4 hexahydropthalimide | [1(S),4S]—1-[3-(acetylthio)-2-methyl-1-oxopropyl]-4-(hexahydro-2H—isoindol-2-yl-1,3-dione)-L-proline |
| 5 1,8 naphthalenecar- | [1(S),4S]—1-[3-(acetylthio)- |

-continued

| Columm I | Column II |
|---|---|
| boximide | 2-methyl-1-oxopropyl]-4-(1,3-dihydro-1,3-dioxo-2H—benz[de]isoquinolin-2-yl)-L-proline |
| 6 saccharin | (1(S),4S]—1-[3-(acetylthio)-2-methyl-1-oxopropyl]-4-(1,-1,3-trioxo-1,2-benzisothiazol-2(3H)—yl)-L-proline |
| 7 succinimide | [1(S),4S]—1-[3-(acetylthio)-2-methyl-1-oxopropyl]-4-(1-pyrrolidinyl-2,5-dione-L-proline |
| 8 glutarimide | [1(S),4S]—1-[3-(acetylthio)-2-methyl-1-oxopropyl]-4-(1-piperidinyl)-2,6-dione-L-proline |
| 9 maleimide | [1(S),4S]—1-[3-(acetylthio)-2-methyl-1-oxopropyl]-4-(2,5-dihydro-2,5-dioxo-1H—pyrrol-1-yl)-L-proline |
| 10 diacetamide | [1(S),4S]—1-[3-(acetylthio)-2-methyl-1-oxopropyl]-4-diacetamido-L-proline |
| 11 dibenzamide | [1(S),4S]—1-[3-(acetylthio)-2-methyl-1-oxopropyl]-4-dibenzamido-L-proline |
| 12 N—acetylbenzamide | [1(S),4S]—1-3-(acetylthio)-2-methyl-1-oxopropyl]-4-(N—acetylbenzamido)-L-proline |
| 13 diphenacetamide | [1(S),4S]—1-[3-(acetylthio)-2-methyl-1-oxopropyl]-4-diphenacetamido-L-proline |
| 14 dicinnamoylamine | [1(S),4S]—1-[3-(acetylthio)-2-methyl-1-oxopropyl]-4-dicinnamoylamino-L-proline |
| 15 dimethylsulfonamide | [1(S),4S]—1-[3-(acetylthio)-2-methyl-1-oxopropyl]-4-dimethylsulfonamido-L-proline |
| 16 dibenzenesulfonamide | [1(S),4S]—1-[3-(acetylthio)-2-methyl-1-oxopropyl]-4-dibenzenesulfonamido-L-proline |
| 17 N—(benzenesulfonyl)-acetamide | [1(S),4S]—1-[3-(acetylthio)-2-methyl-1-oxopropyl]-4-(N—(benzenesulfonyl)acetamido)-L-proline |

EXAMPLES 18–29

Following the procedure of Example 1, but substituting the compound listed in Column I for benzoyl chloride in part F, yields the compound listed in Column II.

| Column I | Column II |
|---|---|
| 18 4-fluorobenzoyl chloride | [1(S),4S]—4-(4-fluorobenzoylamino)-1-(3-mercapto-2-methyl-1-oxopropyl)-L-proline |
| 19 2,6-dichlorobenzoyl chloride | [1(S),4S]—4-(2,6-dichlorobenzoylamino)-1-(3-mercapto-2-methyl-1-oxopropyl)-L-proline |
| 20 2,4,6-trimethylbenzoyl chloride | [1(S),4S]—4-(2,4,6-trimethylbenzoylamino)-1-(3-mercapto-2-methyl-1-oxopropyl)-L-proline |
| 21 3,4 dimethoxybenzoyl chloride | [1(S),4S]—4-(3,4-dimethoxybenzoylamino)-1-(3-mercapto-2-methyl-1-oxopropyl)-L-proline |
| 22 4-ethylthobenzoyl chloride | [1(S),4S]—4-(4-ethylthiobenzoylamino)-1-(3-mercapto-2-methyl-1-oxopropyl)-L-proline |
| 23 2-hroxybenzoyl chloride | [1(S),4S]—4-(2-hydroxybenzoylamino)-1-(3-mercapto-2-methyl-1-oxopropyl)-L-proline |
| 24 4-acetylbenzoyl chloride | [1(S),4S]—4-(4-acetylbenzoylamino)-1-(3-mercapto-2-methyl-1-oxopropyl)-L-proline |
| 25 4-nitrobenzoyl chloride | [1(S),4S]—4-(4-nitrobenzoylamino)-1-(3-mercapto-2-methyl-1-oxopropyl)-L-proline |
| 26 3-fluoro-4-methoxy-benzoyl chloride | [1(S),4S]—4-(3-fluoro-4-methoxybenzoylamino)-1-(3-mercapto-2-methyl-1-oxopropyl)-L-proline |
| 27 4-dimethylaminobenzoyl chloride | [1(S),4S]—4-(4-dimethylaminobenzoylamino)-1-(3-mercapto-2-methyl-1-oxopropyl)-L-proline |
| 28 4-phenylbenzoyl chloride | [1(S),4S]—4-(4-phenylbenzoylamino)-1-(3-mercapto-2-methyl-1-oxopropyl)-L-proline |
| 29 3-trifluoromthylbenzoyl chloride | [1(S),4S]—4-(3-trifluoromethylbenzoylamino)-1-(3-mercapto-2-methyl-1-oxopropyl)-L-proline |

EXAMPLE 30

[1(S),4S]-1-(3-Mercapto-2-methyl-1-oxopropyl)-4-(1-piperidinyl)-L-proline, hydrochloride (A)

[4S]-1-[(Phenylmethoxy)carbonyl]-4-(1-piperidinyl)-L-proline, methyl ester

A mixture of 15.0 g of 1-[(phenylmethoxy)carbonyl]-trans-4-tosyloxy-L-proline, methyl ester (J.A.C.S., 79, 191 (1957)) and 75 ml of piperidine is stirred at room temperature for 24 hours. The excess piperidine is removed under reduced pressure and the residue is dissolved in 50 ml of chloroform. The latter solution is extracted twice with 10 ml portions of water, dried (MgSO₄), filtered and the solvent evaporated to give the title compound.

(B) [4S]-4-(1-Piperidinyl)-L-proline, methyl ester

A solution of 10.0 g of [4S]-1-[(phenylmethoxy)carbonyl]-4-(1-piperidinyl)-L-proline, methyl ester in 100 ml of methanol is treated with a suspension of 2 g of 5% palladium on charcoal in 10 ml of water and placed under 3 atmospheres of hydrogen. After an equivalent quantity of hydrogen is consumed, the suspension is filtered and the solvent evaporated to give the title compound.

(C)

[1(S),4S]-1-[3-(Acetylthio)-2-methyl-1-oxopropyl]-4-(1-piperidinyl)-L-proline, methyl ester, hydrochloride.

A solution of 7.0 g of [4S]-4-(1-piperidinyl)-L-proline, methyl ester in 100 ml of chloroform is stirred and maintained at 20°–25° C. during the addition of an equivalent quantity of (S)-3-(acetylthio)-2-methylpropionyl chloride. After stirring for 4 hours at room temperature, the solvent is removed yielding the title compound.

(D)

[1(S),4S]-1-(3-Mercapto-2-methyl-1-oxopropyl)-4-(1-piperidinyl)-L-proline, hydrochloride. A solution of 5.0 g of [1(S),4S]-1-[3-(acetylthio)-2-methyl-1-oxopropyl]-4-(1-piperidinyl)-L-proline, methyl ester, hydrochloride in 50 ml of dioxane is treated with 3.0 ml of a saturated solution of hydrogen chloride in methanol, and the resulting solution is allowed to stand for 12 hours at 0°–10° C. The solvent is evaporated to give the title compound.

EXAMPLES 31–44

Following the procedure of Example 30, but substituting the compound listed in Column I for piperidine, yields the compound listed in Column II.

| Column I | Column II |
| --- | --- |
| 31 pyrrolidine | [1(S),4S]—1-(3-mercapto-2-methyl-1-oxopropyl)-4-(1-pyrrolidinyl)-L-proline, hydrochloride |
| 32 morpholine | [1(S),4S]—1-(3-mercapto-2-methyl-1-oxopropyl)-4-(4-morpholinyl)-L-proline, hydrochloride |
| 33 4-methylpiperazine | [1(S),4S]—1-(3-mercapto-2-methyl-1-oxopropyl)-4-4-methyl-1-piperazinyl)-L-proline, hydrochloride |
| 34 4-phenylpiperazine | [1(S),4S]—1-(3-mercapto-2-methyl-1-oxopropyl)-4-(4-phenyl-1-piperazinyl)-L-proline, hydrochloride |
| 35 imidazole | [1(S),4S]—1-(3-mercapto-2-methyl-1-oxopropyl)-4-(1-imidazolyl)-L-proline, hydrochloride |
| 36 diethylamine | [1(S),4S]—1-(3-mercapto-2-methyl-1-oxopropyl)-4-(diethylamino)-L-proline, hydrochloride |
| 37 cyclohexylamine | [1(S),4S]—1-(3-mercapto-2-methyl-1-oxopropyl)-4-(cyclohexylamino)-L-proline, hydrochloride |
| 38 1-adamantylamine | [1(S),4S]—1-(3-mercapto-2-methyl-1-oxopropyl)-4-(1-adamantylamino)-L-proline, hydrochloride |
| 39 N—methyl-1-adamantylamine | [1(S),4S —1-(3-mercapto-2-methyl-1-oxopropyl)-4-(N—methyl-1-adamantylamino)-L-proline, hydrochloride |
| 40 t-butylamine | [1(S),4S]—1-(3-mercapto-2-methyl-1-oxopropyl)-4-(t-butylamino)-L-proline, hydrochloride |
| 41 aniline | [1(S),4S]—1-(3-mercapto-2-methyl-1-oxopropyl)-4-(phenylamino)-L-proline, hydrochloride |
| 42 p-chloroaniline | [1(S),4S]—1-(3-mercapto-2-methyl-1-oxopropyl)-4-(4-chlorophenylamino)-L-proline, hydrochloride |
| 43 benzylamine | [1(S),4S]—1-(3-mercapto-2-methyl-1-oxopropyl-4-(benzylamino)-L-proline, hydrochloride |
| 44 phenethylamine | [1(S),4S]—1-(3-mercapto-2-methyl-1-oxopropyl)-4-(phenethylamino)-L-proline, hydrochloride |

EXAMPLES 45–48

Following the procedure of Example 1, but substituting the compound liste in Column I for D-3-(acetylthio)-2-methylpropionyl chloride, yields the compound listed in Column II.

| Column I | Column II |
| --- | --- |
| 45 3-(acetylthio)-2-(trifluoromethyl)propionyl chloride | (4S)—4-(benzoylamino)-1-(3-mercapto-2-trifluoromethyl-1-oxopropyl)-L-proline |
| 46 4-(acetylthio)butyryl chloride | (4S)—4-(benzoylamino)-1 (4-mercapto-1-oxobutyl)-L-proline |
| 47 2-(acetylthio)acetyl chloride | (4S)—4-(benzoylamino)-1-(3-mercapto-1-oxoethyl)-L-proline |
| 48 3-actylthio)-2-(methylthio)propionyl chloride | (4S)—4-(benzoylamino)-1-[3-mercapto-2-methylthio)-1-oxopropyl)-L-proline |

EXAMPLE 49

[1(S),4S]-4-(Benzoylamino)-1-(3-mercapto-2-methyl-1-oxopropyl)-L-proline, sodium salt A suspension of 5.0 g of [1(S),4S]-4-(benzoylamino)-1-(3-mercapto-2-methyl-1-oxopropyl)-L-proline is suspended in 15 ml of water and treated with 1 equivalent of sodium bicarbonate. The solution is evaporated under reduced pressure to give the title compound.

EXAMPLE 50

[1(S),4S]-4-(1-Homopiperidinyl)-1-(3-mercapto-2-methyl-1-oxopropyl)-L-proline

Following the procedure of Example 30, but substituting homopiperidine for piperidine in part A, yields the title compound.

EXAMPLE 51

[1(S),4S]-(3-Mercapto-2-methyl-1-oxopropyl)-4-(1-naphthoylamino)-L-proline

Following the procedure of Example 1, but substituting 1-naphthoyl chloride for benzoyl chloride in part F, yields the title compound.

EXAMPLE 52

[1(S),4S]-(3-Mercapto-2-methyl-1-oxopropyl)-4-(2-naphthoylamino)-L-proline

Following the procedure of Example 1, but substituting 2-naphthoyl chloride for benzoyl chloride in part F, yields the title compound.

EXAMPLE 53

[1(S),1'(S), 4R, 4'R]-1,1'-[Dithiobis(2-methyl-1-oxopropane-3,1-diyl)-bis]4-benzylamino-L-proline A solution of the product from Example 1 is dissolved in ethanol, stirred and treated with a solution of one equivalent of iodine in ethanol. The pH of the solution is maintained at 6–7 by the addition of N-sodium hydroxide solution. The solvent is evaporated and the residue extracted with ethyl acetate. After drying over MgSO$_4$, the solution is filtered and the solvent evaporated to give the title compound.

EXAMPLE 54

[1(S)]-4-(Benzoylamino)-1-(3-mercapto-2-methyl-1-oxopropyl)-DL-pipecolinic acid

Following the procedure of Example 1, but substituting DL-4-hydroxypipecolinic acid for trans-4-hydroxy-L-proline in part A, the title compound is obtained.

What is claimed is:

1. A compound having the formula

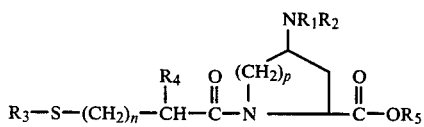

wherein
R$_1$ and R$_2$ together with the nitrogen atom to which they are attached are 1-imidazolyl, 1-pyrrolidinyl-2,5-dione, 3-alkyl-1-pyrrolidinyl-2,5-dione, 3-aryl-1-pyrrolidinyl-2,5-dione, 1-piperidinyl-2,6-dione, 3-alkyl-1-piperidinyl-2,6-dione, 3-aryl-1-piperidinyl-2,6-dione, or 2,5-dihydro-2,5-dioxo-1H-pyrrol-1-yl;
R$_3$ is hydrogen, alkyl, aryl, arylalkyl, alkanoyl or arylcarbonyl;
R$_4$ is hydrogen, alkyl, alkylthio, or trifluoromethyl;
R$_5$ is hydrogen, alkyl or arylalkyl;
n is 0, 1 or 2; and
p is 1 or 2;

or a non-toxic, physiologically acceptable salt thereof, or symmetrical dimer thereof; wherein the term "aryl" refers to phenyl, 1-naphthyl, 2-naphthyl, or phenyl substituted with halogen, alkyl, alkoxy, alkylthio, hydroxy, alkanoyl, nitro, amino, dialkylamino, phenyl or trifluoromethyl groups; the term "alkanoyl" refers to groups having up to 9 carbon atoms; and the terms "alkyl" and "alkoxy" refer to groups having 1 to 8 carbon atoms.

2. A compound in accordance with claim 1 wherein R$_3$ is hydrogen.

3. A compound in accordance with claim 1 wherein R$_4$ is hydrogen.

4. A compound in accordance with claim 1 wherein R$_4$ is alkyl.

5. A compound in accordance with claim 1 wherein R$_4$ is alkylthio.

6. A compound in accordance with claim 1 wheren R$_4$ is trifluoromethyl.

7. A compound in accordance with claim 1 wherein n is 1.

8. A compound in accordance with claim 1 wherein n is 2.

9. A compound in accordance with claim 1 wherein p is 1.

10. A compound in accordance with claim 1 wherein p is 2.

11. A compound in accordance with claim 1 wherein R$_5$ is hydrogen.

12. A compound in accordance with claim 1 wherein n is 1, p is 1, R$_4$ is methyl, and R$_5$ is hydrogen.

* * * * *